(12) United States Patent
Zhang et al.

(10) Patent No.: US 11,207,384 B2
(45) Date of Patent: Dec. 28, 2021

(54) RAPID-ACTING INSULIN COMPOSITIONS

(71) Applicant: Eli Lilly and Company, Indianapolis, IN (US)

(72) Inventors: Jun Zhang, Acton, MA (US); Chad Donald Paavola, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/615,894

(22) PCT Filed: May 31, 2018

(86) PCT No.: PCT/US2018/035261
§ 371 (c)(1),
(2) Date: Nov. 22, 2019

(87) PCT Pub. No.: WO2018/222787
PCT Pub. Date: Dec. 6, 2018

(65) Prior Publication Data
US 2020/0078446 A1 Mar. 12, 2020

Related U.S. Application Data

(60) Provisional application No. 62/513,645, filed on Jun. 1, 2017.

(51) Int. Cl.
| A61K 38/28 | (2006.01) |
|---|---|
| A61P 3/10 | (2006.01) |
| A61K 9/00 | (2006.01) |
| A61K 47/02 | (2006.01) |
| A61K 47/10 | (2017.01) |
| A61K 47/30 | (2006.01) |

(52) U.S. Cl.
CPC .......... *A61K 38/28* (2013.01); *A61K 9/0019* (2013.01); *A61K 47/02* (2013.01); *A61K 47/10* (2013.01); *A61K 47/30* (2013.01); *A61P 3/10* (2018.01)

(58) Field of Classification Search
CPC ........ A61K 33/30; A61K 38/28; A61K 47/10; A61K 47/30; A61K 47/02; A61K 9/0019; A61K 9/0021; A61P 3/10
See application file for complete search history.

(56) References Cited

U.S. PATENT DOCUMENTS

| 4,476,118 A | 10/1984 | Brange et al. |
|---|---|---|
| 4,885,164 A | 12/1989 | Thurow |
| 5,164,366 A | 11/1992 | Balschmidt et al. |
| 5,474,978 A | 12/1995 | Bakaysa et al. |
| 5,547,942 A | 8/1996 | Rapaport |
| 5,716,927 A | 2/1998 | Balschmidt et al. |
| 5,866,538 A | 2/1999 | Norup et al. |
| 7,279,457 B2 | 10/2007 | Pohl et al. |
| 7,696,162 B2 | 4/2010 | Boderke |
| 7,713,930 B2 | 5/2010 | Brunner-Schwarz et al. |
| 8,084,420 B2 | 12/2011 | Steiner et al. |
| 8,318,154 B2 | 11/2012 | Frost et al. |
| 8,591,465 B2 * | 11/2013 | Hommann .......... A61M 5/2033 604/131 |
| 9,439,952 B2 | 9/2016 | Christe et al. |
| 9,901,623 B2 | 2/2018 | Akers et al. |
| 9,993,555 B2 | 6/2018 | Akers et al. |
| 2002/0028786 A1 | 3/2002 | Frey et al. |
| 2007/0086952 A1 | 4/2007 | Steiner et al. |
| 2007/0235365 A1 | 10/2007 | Pohl et al. |
| 2008/0090753 A1 | 4/2008 | Pohl et al. |
| 2010/0167990 A1 | 7/2010 | Poulsen et al. |
| 2010/0227795 A1 | 9/2010 | Steiner et al. |
| 2010/0249020 A1 | 9/2010 | Soula et al. |
| 2012/0094902 A1 | 4/2012 | Soula et al. |
| 2012/0178675 A1 | 7/2012 | Pohl et al. |
| 2013/0011378 A1 | 1/2013 | Yang et al. |
| 2013/0022592 A1 | 1/2013 | Vaughn et al. |
| 2013/0231281 A1 | 9/2013 | Soula et al. |
| 2013/0302275 A1 | 11/2013 | Wei et al. |
| 2014/0113856 A1 | 4/2014 | Pohl et al. |
| 2014/0135682 A1 | 5/2014 | Frost et al. |
| 2014/0357554 A1 | 12/2014 | Pohl et al. |
| 2015/0065423 A1 | 3/2015 | Laulicht et al. |
| 2015/0273022 A1 | 10/2015 | Wilson et al. |
| 2016/0082106 A1 | 3/2016 | Soule et al. |
| 2016/0166695 A1 | 6/2016 | Akers et al. |
| 2017/0056478 A1 | 3/2017 | Akers et al. |
| 2018/0078645 A1 | 3/2018 | Gerring et al. |
| 2018/0221385 A1 | 8/2018 | Ardilouze et al. |

FOREIGN PATENT DOCUMENTS

| EP | 0214826 A2 | 8/1986 |
|---|---|---|
| EP | 0280534 A2 | 2/1988 |
| WO | 199733531 A1 | 9/1997 |
| WO | 199749386 A1 | 12/1997 |
| WO | 199934821 A1 | 7/1999 |
| WO | 200043034 A2 | 7/2000 |

(Continued)

OTHER PUBLICATIONS

Pohl, R., et al. (2012). Ultra-rapid absorption of recombinant human insulin induced by zinc chelation and surface charge masking. 6(4), pp. 755-563.

Pohl, et al., "Development of Ultra-Rapid-Acting Prandial Insulin analogs Requires Chelation of Zinc Ions and Charge Masking to Increase the Rate of Subcutaneous Absorption," available at http://files.shareholder.com/downloads/BIOD/0x0x602912/3C955886-6AA4-4D66-BD33-3FFB4C906B25/EASD_Poster_September_2012_FINAL.pdf (2012).

(Continued)

Primary Examiner — Marcela M Cordero Garcia
(74) Attorney, Agent, or Firm — Matthew T. Lord

(57) ABSTRACT

The invention is a composition of insulin or insulin analog that has faster pharmacokinetic action than commercial formulations of rapid-onset insulin analog products.

14 Claims, No Drawings

Specification includes a Sequence Listing.

(56) References Cited

FOREIGN PATENT DOCUMENTS

| WO | 200135943 A2 | 5/2001 |
| --- | --- | --- |
| WO | 2003000202 A2 | 1/2003 |
| WO | 2010102020 A1 | 9/2010 |
| WO | 2012006283 A1 | 1/2012 |
| WO | 2013158618 A1 | 10/2013 |
| WO | 2015106269 A2 | 7/2015 |
| WO | 2015120457 A1 | 8/2015 |
| WO | 2017015760 A1 | 2/2017 |
| WO | 2017191464 A1 | 11/2017 |
| WO | 2018023060 A2 | 11/2018 |
| WO | 2018203059 A1 | 11/2018 |
| WO | 2018203061 A1 | 11/2018 |

OTHER PUBLICATIONS

Krasner, et al., "Lispro Formulations BIOD-238 and BIOD-250 Associated With Faster Absorption and Declines From Peak Concentrations Compared to Humalog®" available at http://files.shareholder.com/downloads/BIOD/2632769718x0x672700/BF867032-C746-4DB1-A80B-FFA9DE1E565B/Lispro_Formulations_BIOD-238_and_BIOD-250_Associated_With_Faster_Absorption_-_ADA_June_2013.PDF (2013).

Capelle, M. A., Gurny, R., & Arvinte, T. (2007). High throughput screening of protein formulation stability: practical considerations. *European journal of pharmaceutics and biopharmaceutics*, 65(2), 131-148.

Prabhu, S., Jacknowitz, A. I., & Stout, P. J. (2001). A study of factors controlling dissolution kinetics of zinc complexed protein suspensions in various ionic species. *International journal of pharmaceutics*, 217(1), 71-78.

International Search Report and Written Opinion of the International Searching Authority pertaining to International Application No. PCT/US2018/035261; Filing Date: May 13, 2018; dated Sep. 12, 2018.

Jintapattanakit, A., Kissel, T., & Junyaprasert, V. B. (2008). Effect of tripolyphosphate on physical and enzymatic stabilities of insulin loaded nanoparticles of N-trimethyl chitosan. *Mahidol Univ J Pharm Sci*, 35, 1-7.

Grenha, A., Seijo, B., & Remunán-López, C. (2005). Microencapsulated chitosan nanoparticles for lung protein delivery. *European journal of pharmaceutical sciences*, 25(4-5), 427-437.

\* cited by examiner

RAPID-ACTING INSULIN COMPOSITIONS

The present invention is a pharmaceutical insulin composition for parenteral injection to counteract prandial and post-prandial blood glucose excursions. The composition includes an insulin and a polyphosphate compound, and has faster uptake of insulin from injection sites than existing commercial insulin compositions. The composition is useful for rapidly providing insulin activity when insulin is needed, e.g., when food is consumed.

Diabetes mellitus is a chronic disorder characterized by hyperglycemia resulting from defects in insulin secretion, insulin action, or both. Type 1 diabetes mellitus is characterized by little or no insulin secretory capacity, and patients with type 1 diabetes mellitus require insulin for survival. In type 2 diabetes mellitus, the combined effects of impaired insulin secretion and insulin resistance result in elevated blood glucose levels. In at least one-third of patients with type 2 diabetes mellitus the disease progresses to an absolute requirement for insulin therapy.

The time-action profile of insulin is important for controlling post-prandial blood glucose levels. In healthy individuals, the pancreas secretes a spike of insulin in response to absorbed food, which results in increased blood insulin levels within several minutes. In individuals with type 1 diabetes and in certain individuals with type 2 diabetes, insulin must be administered. However, administered insulin enters the blood more slowly than endogenously secreted insulin, and slow onset may result in hyperglycemia during the early postprandial period. Too long duration of action can result in excessive insulin between meals which results in late postprandial hypoglycemia and/or weight gain.

There have been previous attempts to accelerate the time-action of insulin products. The "rapid-acting" insulin analogs became available in the 1990s and early 2000s. Even with so-called "rapid-acting" insulin analogs, such as insulin lispro (HUMALOG®), insulin aspart (NOVOLOG®) and insulin glulisine (APIDRA®), the maximum circulating insulin concentration is not reached until 50-90 minutes following the injection. This is not rapid enough to match carbohydrate absorption profiles.

Research has been conducted more recently in attempts to develop a product with more rapid time action profile than those described above. For example, US2014/0378383 discloses insulin compositions containing a combination of a substituted anionic compound consisting of a saccharide backbone formed from between 1 and 8 hexose saccharide units having partially substituted carboxyl functional groups with a polyanionic compound, and states that such a combination makes it possible to accelerate the passage of the insulin into the blood. Similarly, US2015/0231160 discloses insulin compositions containing a combination of an oligosaccharide and a polyanionic compound, and states this combination allows a significant reduction in the time for the start of action of a formulation of rapid-acting insulin analog. These disclosures each describe an array of polyanionic compounds, including polyphosphoric acids such as triphosphate, but no compositions are described which contain triphosphate but do not also contain either a substituted anionic compound, as that term is used in US2014/0378373, or an oligosaccharide, as described in US2015/0231160, and no data are provided on the pharmacokinetics or pharmacodynamics of compositions containing triphosphate or any other polyphosphoric acid. US2014357554 and US2015273022 describe compositions said to have rapid onset of insulin action which contain EDTA, citrate, and magnesium containing compounds, one example of which is magnesium pyrophosphate. The magnesium compound is stated to minimize injection site irritation "but not change the rate of subcutaneous absorption," and no data on compositions containing magnesium pyrophosphate are described.

There remains a need for compositions of insulin, intended for use at meal-time, that have more rapid uptake of insulin from the injection site and more rapid onsets of action than existing commercial insulin products.

The present invention seeks to meet these needs by providing pharmaceutically-acceptable, formulations of insulin that have more rapid uptake of insulin into the blood and more rapid onset of action than existing commercial insulin products.

According to a first aspect of the present invention, there is provided a pharmaceutical composition comprising an insulin and a polyphosphate compound selected from the group consisting of pyrophosphate, trimetaphosphate, triphosphate, and tetraphosphate, provided that the composition does not contain either a saccharide multimer or EDTA.

In certain embodiments, the concentration of polyphosphate is from about 5 to about 50 mM. In certain embodiments, the concentration of polyphosphate is about 10 to about 30 mM. In certain embodiments, the concentration of polyphosphate is about 20 to about 25 mM. In certain embodiments, the concentration of polyphosphate is selected from the group consisting of 5, 10, 15, 20, 25 or 30 mM.

In certain embodiments, the composition further comprises zinc. In certain embodiments, the zinc concentration is from about 0.2 to about 5 mM.

In certain embodiments, the composition further comprises a tonicity agent. In certain embodiments, the tonicity agent is glycerol.

In certain embodiments, the composition further comprises one or more preservatives. In certain embodiments, the one or more preservatives are selected from the group consisting of phenol, meta-cresol, and benzyl alcohol.

In certain embodiments, the insulin is selected from the group consisting of human insulin, insulin lispro, insulin aspart and insulin glulisine. In certain embodiments, the insulin concentration is from about 40 to about 500 IU/mL. In certain embodiments, the insulin concentration is from about 100 to about 200 IU/mL.

According to another aspect of the present invention, there is provided a method of treating diabetes comprising administering to a human in need thereof an effective dose of one of the above-described compositions.

According to another aspect of the present invention, there is provided one of the above-described compositions for use as a medicament.

According to another aspect of the present invention, there is provided one of the above-described compositions for use in the treatment of diabetes.

According to another aspect of the present invention, there is provided an article of manufacture comprising one of the above-described compositions. In certain embodiments, the article of manufacture is a multi-use vial. In certain embodiments, the article of manufacture is a pre-filled, disposable pen. In certain embodiments, the article of manufacture is a re-usable pen. In certain embodiments, the article of manufacture is an autoinjector. In certain embodiments, the article of manufacture is a pump for continuous subcutaneous insulin infusion (CSII).

When used herein, "saccharide multimer" means any compound containing more than one saccharide unit bound together, including for example the substituted anionic compounds described in US2014/0378383 and the oligosaccharides described in US2015/0231160.

When used herein, the term "does not contain a saccharide multimer or EDTA" means that the composition contains no saccharide multimers or EDTA, or contains only a de minimis quantity of saccharide multimers or EDTA such that the time action profile of the insulin is unaffected.

When used herein, "insulin" means human insulin or a structural variant, mutant, or analog of human insulin that has the functional activity of human insulin. Analogs of human insulin include but are not limited to insulin lispro, insulin aspart, and insulin glulisine, or other "rapid-acting" insulin analogs. Insulin for commercial products may be produced using recombinant DNA methods or by chemical synthesis. Recombinant methods are well-known and are strongly preferred. A molecule of human insulin (CAS No. 11061-68-0) consists of two amino acid chains, A and B, whose sequences are well-known. The chains are joined by two disulfide bonds: CysA7-CysB7 and CysA20-CysB19. The A-chain has an intra-chain disulfide bond at CysA6-CysA11.

The human insulin A-chain has the following sequence of amino acids:

(SEQ ID NO: 1)
Gly Ile Val Glu Gln Cys Cys Thr Ser Ile Cys Ser

Leu Tyr Gln Leu Asn Tyr Cys Asn

The human insulin B-chain has the following sequence of amino acids:

(SEQ ID NO: 2)
Phe Val Asn Gln His Leu Cys Gly Ser His Leu Val

Glu Ala Leu Tyr Leu Val Cys Gly Glu Arg Gly Phe

Phe Tyr Thr Pro Lys Thr.

Insulin lispro (CAS No. 133107-64-9), the drug substance in HUMALOG®, has been shown to be equipotent to human insulin on a molar basis but its effect after subcutaneous injection is more rapid and of shorter duration than that of injected soluble human insulin. A consistent pattern of kinetics with a shorter Tmax and half-life and with a higher Cmax was observed for insulin lispro when compared to the human insulin. Insulin lispro is biologically equivalent to insulin in several in vitro tests including insulin receptor binding in cultured lymphocytes, human placenta and human liver, and glucose transport in adipocytes. HUMALOG® contains m-cresol as a preservative and a stabilizer, a tonicity modifier (glycerin), a buffering agent (dibasic sodium phosphate), a stabilizer (zinc oxide) and pH adjustment for the vehicle.

A molecule of insulin lispro consists of the human insulin A-chain cross-linked with the insulin lispro B-chain, whose amino acid sequence is given by SEQ ID NO:3, below:

(SEQ ID NO: 3)
Phe Val Asn Gln His Leu Cys Gly Ser His Leu Val

Glu Ala Leu Tyr Leu Val Cys Gly Glu Arg Gly Phe

Phe Tyr Thr Lys Pro Thr.

One unit of insulin lispro is equivalent to 0.0347 mg insulin lispro.

Insulin aspart (CAS No. 116094-23-6), the drug substance in NOVOLOG®, is another rapid-onset insulin analog. Its structure consists of the A-chain of human insulin and a B-chain analog as reflected in the following amino acid sequence:

(SEQ ID NO: 4)
Phe Val Asn Gln His Leu Cys Gly Ser His Leu Val

Glu Ala Leu Tyr Leu Val Cys Gly Glu Arg Gly Phe

Phe Tyr Thr Asp Lys Thr.

One unit of insulin aspart corresponds to 6 nmol, corresponding with 0.035 mg salt-free anhydrous insulin aspart.

Insulin glulisine (CAS No. 207748-29-6), the drug substance in APIDRA®, is yet another rapid-onset insulin analog. A molecule of insulin glulisine consists of human insulin A-chain and a modified B-chain compared with human insulin, as reflected in the following amino acid sequence:

(SEQ ID NO: 5)
Phe Val Lys Gln His Leu Cys Gly Ser His Leu Val

Glu Ala Leu Tyr Leu Val Cys Gly Glu Arg Gly Phe

Phe Tyr Thr Pro Glu Thr.

One unit of insulin glulisine corresponds approximately to 0.0349 mg of insulin glulisine.

The compositions of the present invention have concentrations of insulin between 0.24 and 3 mM (40-500 IU/mL; 1.4 mg/mL-17.5 mg/mL). The compositions of the present invention are likely to have specific concentrations of 40, 100, 200, 300, 400, and 500 IU/mL (1.4, 3.5, 7, 10.5, 14, and 17.5 mg/mL). Preferred concentrations are 100 and 200 IU/mL.

Polyphosphates are inorganic, multi-charged, polyvalent anions consisting of 2 or more phosphate groups covalently bonded via P—O—P bonds. They are widely used in detergents, foods, cosmetics, and biomedical applications as chelating agents, buffers, and cross-linking agents, among other uses. A number of polyphosphates are "generally regarded as safe" by the U.S. Food and Drug Administration for use in foods ("GRAS"), including for example those listed in Table 1 below.

TABLE 1

Examples of GRAS polyphosphates.

| GRAS Substance | Formula (m.w.) | CAS No. | 21 CFR |
|---|---|---|---|
| Calcium pyrophosphate | $Ca_2P_2O_7$ (254.1) | 7790-76-3 | 182.8223 |
| Potassium pyrophosphate | $K_4P_2O_7$ (330.3) | 7320-34-5 | None |
| Potassium tripolyphosphate | $K_5P_3O_{10}$ (453.5) | 13845-36-8 | None |
| Sodium acid pyrophosphate | $Na_2H_2P_2O_7$ (221.9) | 7758-16-9 | 182.1087 |
| Sodium pyrophosphate | $Na_4P_2O_7$ (265.9) | 7722-88-5 | 182.6760 |
| Sodium tetraphosphate | $Na_6P_4O_{13}$ (469.8) | 14986-84-6 | None |
| Sodium trimetaphosphate | $Na_3P_3O_9$ (305.9) | 7785-84-4 | None |
| Sodium tripolyphosphate | $Na_5P_3O_{10}$ (367.9) | 7758-29-4 | 182.1810 |
| | | | 182.1610 |

Triphosphate has been used as a cross-linking agent in polymer-based nanocarriers, especially chitosan-based nanocarriers, for oral, nasal, parenteral, or transdermal delivery of a large range of medically-important payloads, such as antigens, anti-cancer drugs, genetic materials, and proteins, including insulins. Kouchak, et al., "Effect of different molecular weights of chitosan on preparation and characterization of insulin loaded nanoparticles by ion gelation method," 4 Internat'l J. Drug Dev. & Res. 271 (2012). Unlike the present invention, however, such carriers are not directed towards accelerating the time action profile of administered insulin.

The polyphosphates shown herein to be useful for increasing the rate of insulin absorption from injection sites are pyrophosphate (diphosphate, $[O_3-P-O-P-O_3]^{-4}$, $P_2O_7$) and triphosphate ($[O_3-P-O-(PO_2)-O-P-O_3]^{-5}$, $P_3O_{10}$). The effects on insulin absorption are believed to be provided by these polyphosphates as well as trimetaphosphate $(P_3O_9)^-$ and tetraphosphate $(P_4O_{13}^{-6})$. The particular polyphosphate compound used may be the acidic form or various salt forms, especially the alkali (e.g., sodium and potassium) salts. Pyrophosphate, triphosphate, trimetaphosphate and tetraphosphate, and their various salts, especially their alkali (e.g., sodium and potassium) and alkaline earth metal (e.g., calcium and magnesium) salts may be used in the present invention. Of these, triphosphate and salts thereof are preferred. The concentration of polyphosphate in the compositions ranges from 5 mM to 50 mM, particularly 5, 10, 15, 20, 25, 30, 35, 40 or 50 mM. Certain compositions have polyphosphate concentrations in the range of 10 mM to 30 mM. Certain compositions have polyphosphate concentrations in the range of 15 mM to 25 mM.

Commercial insulin compositions have about 2.4 atoms of zinc per six molecules of insulin (HUMULIN® R U-500), and some have about 3.0 atoms of zinc per six molecules of insulin (HUMALOG®, NOVOLOG®). Certain embodiments of the present invention include zinc in a concentration sufficient to provide between about 2-4 zinc atoms per six molecules of insulin. Other embodiments include zinc in a concentration of up to about 5 mM. In certain embodiments, the concentration of zinc ranges from about 0.2 to about 5 mM. In certain embodiments, the concentration of zinc ranges from about 0.5 to about 2 mM. In certain embodiments, the concentration of zinc is selected from the group consisting of 0.2, 0.3, 0.4, 0.5, 0.6, 0.7, 0.8, 0.9, 1, 1.3 and 2 mM.

The compositions are sterile when first produced. When provided in a multi-use vial or cartridge, an anti-microbial preservative compound or mixture of compounds that is compatible with the other components of the formulation is typically added at sufficient strength to meet regulatory and pharmacopoeial anti-microbial preservative requirements. See U.S. Pharmacopeia Monographs. Insulin lispro injection. USP29-NF24; British Pharmacopeia Monographs 2008 Volume III: Insulin aspart injection; U.S. Pharmacopeia Monographs. Insulin assays; and U.S. Pharmacopeia general chapters. USP29-NF24. Rockville, Md.: U.S. Pharmacopeial Convention; 2005. Antimicrobial effectiveness testing; pp. 2499-2500. Preferred preservatives are aryl acids and phenolic compounds, or mixtures of such compounds. Preservatives most commonly used in insulin products are phenol, m-cresol, and benzyl alcohol. Effective concentrations can be ascertained readily using the methods referenced above. Present commercial compositions, for example, contain 3.15 mg/mL m-cresol (HUMALOG® and APIDRA®)), 1.72 mg/mL m-cresol and 1.50 mg/mL phenol (NOVOLOG®), and 2.5 mg/mL m-cresol (HUMULIN® R U-500).

The pH of insulin compositions of the present invention is typically 7.0 to 7.8 and it is adjusted using physiologically appropriate acids and bases, typically hydrochloric acid 10% and sodium hydroxide 10%. The pH for commercial insulin formulations is usually in the range 7.2 to 7.6, with 7.4±0.1 as a common target pH.

It is desirable to approximately match the tonicity (i.e., osmolality) of body fluids at the injection site as closely as possible when administering the compositions because solutions that are not approximately isotonic with body fluids can produce a painful stinging sensation when administered. Thus, it is desirable that the compositions be approximately isotonic with body fluids at the sites of injection. If the osmolality of a composition in the absence of a tonicity agent is sufficiently less than the osmolality of the tissue (for blood, about 300 mOsmol/kg; the European Pharmacopeial requirement for osmolality is >240 mOsm/kg), then a tonicity agent should generally be added to raise the tonicity of the composition to about 300 mOsmol/kg. Typical tonicity agents are glycerol (glycerin) and sodium chloride. The amount of tonicity agent to add is readily determined using standard techniques. Remington: The Science and Practice of Pharmacy, David B. Troy and Paul Beringer, eds., Lippincott Williams & Wilkins, 2006, pp. 257-259; Remington: Essentials of Pharmaceutics, Linda Ed Felton, Pharmaceutical Press, 2013, pp. 277-300.

The compositions of the present invention are typically administered subcutaneously, either in multiple daily injections (MDI) from a pre-filled, disposable pen, reusable pen, automatic pen injector, multi-use vial or a pump for CSII.

Additional embodiments of the present invention include those described below:

1. A pharmaceutical composition comprising an insulin and a polyphosphate compound selected from the group consisting of pyrophosphate, triphosphate, trimetaphosphate and tetraphosphate.

2. The pharmaceutical composition of any of the above embodiments wherein the composition does not contain either a saccharide multimer or EDTA.

3. The pharmaceutical composition of any of the above embodiments wherein the polyphosphate compound is triphosphate.

4. The pharmaceutical composition of any of the above embodiments wherein the polyphosphate compound is pyrophosphate.

5. The pharmaceutical composition of any of the above embodiments wherein the concentration of the polyphosphate is from about 5 to about 50 mM.

6. The pharmaceutical composition of any of the above embodiments wherein the concentration of the polyphosphate is from about 10 to about 30 mM.

7. The pharmaceutical composition of any of the above embodiments wherein the concentration of the polyphosphate is selected from the group consisting of 5, 10, 15, 20, 25, 30, 35, 40 and 50 mM.

8. The pharmaceutical composition of any of the above embodiments further comprising zinc.

9. The pharmaceutical composition of any of the above embodiments wherein the zinc concentration is from about 0.2 to about 5 mM.

10. The pharmaceutical composition of any of the above embodiments wherein the concentration of zinc ranges from about 0.5 to about 2 mM.

11. The pharmaceutical composition of any of the above embodiments wherein the concentration of zinc is selected from the group consisting of 0.2, 0.3, 0.4, 0.5, 0.6, 0.7, 0.8, 0.9, 1, 1.3, 2 and 5 mM.

12. The pharmaceutical composition of any of the above embodiments further comprising a tonicity agent.

13. The pharmaceutical composition of any of the above embodiments further comprising a tonicity agent which is glycerol.

14. The pharmaceutical composition of any of the above embodiments further comprising one or more preservatives.

15. The pharmaceutical composition of any of the above embodiments wherein the one or more preservatives are selected from the group consisting of phenol, meta-cresol, and benzyl alcohol.

16. The pharmaceutical composition of any of the above embodiments wherein the insulin is selected from the group consisting of human insulin, insulin lispro, insulin aspart and insulin glulisine.

17. The pharmaceutical composition of any of the above embodiments wherein the insulin concentration is from about 40 to about 500 IU/mL.

18. The pharmaceutical composition of any of the above embodiments wherein the insulin concentration is from about 100 to about 200 IU/mL.

19. A method of treating diabetes comprising administering to a human in need thereof an effective dose of the pharmaceutical composition of any of the above embodiments.

20. The pharmaceutical composition of any of the above embodiments for use as a medicament.

21. The pharmaceutical composition of any of the above embodiments for use in the treatment of diabetes.

22. The pharmaceutical composition of any of the above embodiments comprising a mixture of two or more polyphosphate compounds selected from the group consisting of pyrophosphate, triphosphate, trimetaphosphate and tetraphosphate.

23. An article of manufacture comprising any one of the above-described pharmaceutical compositions.

24. A multi-use vial containing any one of the above-described pharmaceutical compositions.

25. A re-usable pen injector containing any one of the above-described pharmaceutical compositions.

26. A pre-filled, disposable pen injector containing any one of the above-described pharmaceutical compositions.

27. An automatic pen injector containing any one of the above-described pharmaceutical compositions.

28. A pump for CSII containing any one of the above-described pharmaceutical compositions.

Pharmacokinetic (PK) and Pharmacodynamic (PD) Studies

Study 1. 25 mM Pyrophosphate or 25 mM Triphosphate

Fifteen diabetic (alloxan induced), castrated, male Yucatan miniature swine (average age 17 months old and average body weight 40 kgs) with previously fitted vascular access ports are used. The diabetic animals are housed individually and have ad lib access to fresh water at all times. They are fed two meals per day of house diet S-9 and receive appropriate maintenance basal and prandial insulin twice per day to manage their diabetic condition.

Test articles (Formulation A and B) are formulated and shipped overnight on cold packs to the study site. They are stored refrigerated until time of dosing and then returned to the refrigerator after dosing of all animals was complete. During the dosing period the test articles remain in an insulated box when not being withdrawn from. HUMALOG® insulin control is from a commercial vial.

TABLE 2

Compositions of test and control articles.

| Formulation Name | Formulation Composition |
|---|---|
| HUMALOG | 3.5 mg/mL insulin lispro |
|  | 7 mM sodium phosphate |
|  | 0.3 mM |
|  | 3.15 mg/mL m-cresol |
|  | 16 mg/mL glycerin |
|  | pH 7.4 |
| insulin lispro + 25 mM Pyrophosphate (Formulation A) | 92 U/mL insulin lispro (3.2 mg/mL) |
|  | 7 mM sodium phosphate |
|  | 0.3 mM zinc |
|  | 3.15 mg/mL m-cresol |
|  | 6.33 mg/mL glycerin |
|  | 25 mM sodium pyrophosphate |
|  | pH 7.4 |
| insulin lispro + 25 mM Triphosphate (Formulation B) | 94 U/mL insulin lispro (3.3 mg/mL) |
|  | 7 mM sodium phosphate |
|  | 0.3 mM zinc |
|  | 3.15 mg/mL m-cresol |
|  | 4.49 mg/mL glycerin |
|  | 25 mM sodium triphosphate |
|  | pH 7.4 |

The study is designed as a three-way cross-over design. This design allows for each individual animal to receive each of the three test articles by dosing one test article each study date (3 dates each 7 days apart). The day prior to study, animals are fed half their daily ration and received 0.2 U/kg Humalog Mix 75/25 Insulin at their morning maintenance administration. All study animals are food-fasted overnight and do not receive their evening insulin or meal prior to drug administration on study day.

On the morning of study, all animals are placed into slings for restraint and have their vascular access ports accessed (equipped for blood sampling) and checked for patency. The animals are randomly placed into treatment groups (3 groups n=5 per group yields n=15 per treatment).

After two baseline blood samples are collected (−30 and −20 min), the animals are returned to their pens and fed ~300 g S-9 diet. Twenty minutes after the presentation of the fully consumed meal, the animals are injected with test article subcutaneously in the flank (0 min) with a Terumo insulin syringe (0.5 ml ½" needle). Dosing involves a single injection of 0.2 U/kg of insulin activity. All study animals have ad libitum access to clean, fresh water throughout the remaining blood collection period.

Serial blood samples (2.0 mL each) are collected from each animal at the following time points: −30, −20 (then immediately Fed), 0 (just before dose), 5, 10, 15, 30, 45, 60, 75, 90, 105, 120, 150, 180, 240, and 360 minutes following the SC dosing. Blood samples (anticoagulant: none [serum]) are maintained at ambient temperature for at least 30 minutes but no more than 2 hours to allow for clotting. Serum is then separated by centrifugation and divided into two aliquots and stored frozen at approximately −70° C.

Serum glucose concentrations are determined using an automated Cobas c311 Clinical Chemistry Analyzer (Roche Diagnostics, Indianapolis). Two animals are excluded from the Humalog treatment group yielding n=13 for that test article. One animal is excluded due to not meeting the criteria for baseline glucose of >200 mg/dL and another animal did not participate due to port patency issues. Serum glucose concentrations (mg/dL) after treatment with insulin lispro-containing formulations (0.2 U/kg at time 0) are provided in Table 3 below.

TABLE 3

Serum glucose concentrations (mg/dL).

| Time (min) | Humalog (n = 13) | | Formulation A (n = 15) 25 mM pyrophosphate | | Formulation B (n = 15) 25 mM triphosphate | |
|---|---|---|---|---|---|---|
| | Average | St. dev. | Average | St. dev. | Average | St. dev. |
| −30 | 293 | 46 | 270 | 77 | 292 | 43 |
| −20 | 297 | 47 | 293 | 40 | 299 | 46 |
| 0 | 322 | 52 | 304 | 48 | 306 | 45 |
| 5 | 325 | 45 | 312 | 52 | 309 | 48 |
| 10 | 313 | 51 | 245 | 48 | 238 | 50 |
| 15 | 285 | 60 | 201 | 47 | 189 | 53 |
| 30 | 216 | 80 | 133 | 56 | 108 | 56 |
| 45 | 165 | 80 | 99 | 63 | 70 | 51 |
| 60 | 131 | 87 | 70 | 45 | 52 | 54 |
| 75 | 104 | 80 | 57 | 39 | 44 | 52 |
| 90 | 83 | 70 | 44 | 35 | 35 | 42 |
| 105 | 68 | 62 | 40 | 33 | 34 | 36 |
| 120 | 58 | 52 | 37 | 34 | 35 | 38 |
| 150 | 49 | 43 | 38 | 38 | 38 | 27 |
| 180 | 48 | 40 | 47 | 48 | 44 | 33 |
| 240 | 69 | 44 | 70 | 73 | 74 | 59 |
| 360 | 143 | 73 | 113 | 87 | 151 | 106 |

Serum insulin concentrations are determined using a competitive radioimmunoassy (RIA). In the RIA, which measures both endogenous pig insulin and exogenous insulin, serum insulin displaced 125I-insulin for binding to guinea pig anti-rat insulin. The antibody complex is precipitated with a goat anti-guinea pig IgG serum reagent. The upper and lower limits of quantitation of the RIA are 5000 and 20 pM, respectively, in heat-treated charcoal-stripped serum. Non-compartmental pharmacokinetic analysis is performed using Phoenix WinNonLin 6.3. Values below the lower limit of quantitation are assigned a value of 20 pM for calculations. Samples above the upper limit of quantitation are either diluted and reanalyzed or were ignored. As noted above, one animal from the HUMALOG treatment did not participate in the study due to port patency issues, yielding n=14 for that test article.

TABLE 4

PK data.

| Formulation | | Tmax (min) | Cmax (nM) | AUC∞ (min*nM) | CL/F (mL/min/kg) |
|---|---|---|---|---|---|
| Humalog (n = 14) | Mean ± SE | 61.1 ± 11.1 | 1.30 ± 0.25 | 141 ± 21.2 | 12.1 ± 1.97 |
| | Median | 45.0 | 1.08 | 142 | 8.43 |
| Formulation A (n = 15) 25 mM Pyrophosphate | Mean ± SE | 32.3 ± 7.6 | 1.29 ± 0.12 | 113 ± 10.7 | 10.6 ± 1.12 |
| | Median | 30.0 | 1.30 | 107 | 11.1 |
| Formulation B (n = 15) 25 mM Triphosphate | Mean ± SE | 14.3 ± 1.88 | 2.93 ± 0.34 | 220 ± 31.4 | 6.88 ± 0.764 |
| | Median | 15.0 | 2.53 | 159 | 7.56 |

Abbreviations = Tmax—time at maximal concentration, Cmax—maximal concentration, AUCINF—area under the curve from 0 to infinity, CL/F—clearance/bioavailability.

The PK/PD data demonstrate that pyrophosphate or triphosphate accelerated time-action and reduced Tmax as compared with HUMALOG. Formulation A with pyrophosphate had Tmax that was ~47% faster than HUMALOG (~33% faster by median Tmax) and had a comparable mean Cmax to HUMALOG. Formulation B with triphosphate had ~77% faster mean Tmax than HUMALOG (~67% faster in median Tmax) and ~125% higher Cmax than Humalog. Formulations containing 25 mM pyrophosphate or 25 mM triphosphate caused faster Tmax and higher Cmax as compared with HUMALOG.

Study 2. Effect of Triphosphate Concentration on PK/PD

Fourteen diabetic (Alloxan induced), castrated, male Yucatan miniature swine (average age 14 mos old and average body weight 35 kgs) with previously fitted vascular access ports are used. The diabetic animals are housed individually and have ad lib access to fresh water at all times. They are fed two meals per day of house diet S-9 and receive appropriate maintenance basal and prandial insulin twice per day to manage their diabetic condition.

Test articles are formulated and shipped overnight on cold packs. They are stored refrigerated until time of dosing and then returned to the refrigerator after dosing of all animals was complete. During the dosing period the test articles remained in an insulated box when not being withdrawn from. HUMALOG control is a commercial vial.

TABLE 5

Compositions of test and control articles.

| Formulation Name | Formulation Composition |
|---|---|
| HUMALOG | 3.5 mg/mL insulin lispro |
| | 7 mM sodium phosphate, pH 7.4 |
| | 0.3 mM Zn molecules |
| | 16 mg/mL glycerin |
| | 3.15 mg/mL m-cresol |
| Formulation C: | 3.5 mg/mL insulin lispro |
| insulin lispro + 5 mM | 7 mM sodium phosphate |
| triphosphate | 0.3 mM zinc |
| | 13.70 mg/mL glycerin |
| | 3.15 mg/mL m-cresol |
| | 5 mM sodium triphosphate, pH 7.4 |
| Formulation D: | 3.5 mg/mL insulin lispro |
| insulin lispro + 10 mM | 7 mM sodium phosphate |
| triphosphate | 0.3 mM zinc |
| | 11.40 mg/mL glycerin |
| | 3.15 mg/mL m-cresol |
| | 10 mM sodium triphosphate, pH 7.4 |
| Formulation E: | 3.5 mg/mL insulin lispro |
| insulin lispro + 20 mM | 7 mM sodium phosphate |
| triphosphate | 0.3 mM zinc |
| | 6.79 mg/mL glycerin |
| | 3.15 mg/mL m-cresol |
| | 20 mM sodium triphosphate, pH 7.4 |

The study is designed a four-way cross over design allowing for each individual animal to receive each of the three test articles and the control by dosing one test article on each study date (4 dates each, 7 days apart).

The day prior to study, animals are fed half their daily ration and received 0.2 U/kg Humalog Mix 75/25 Insulin at their morning maintenance administration. All study animals are food-fasted overnight and do not receive their evening insulin or meal prior to drug administration on study day.

On the morning of study, all animals are placed into slings for restraint and have their vascular access ports accessed (equipped for blood sampling) and checked for patency. The animals are randomly placed into treatment groups (4 groups n=3-4 per group yields n=14 per treatment). Two pigs are never on study due to being on vet observation which caused a total n=14 to be reduced to n=12 prior to any other exclusions. One animal is excluded from the HUMALOG group and two animals are excluded from the insulin lispro+ Triphosphate 10 mM group for not meeting inclusion criteria, thereby yielding n=11 and n=10 respectively for those groups.

After two baseline blood samples are collected (−30 and −20 min), the animals are returned to their pens and fed ~300 g S-9 diet. Twenty minutes after the presentation of the fully consumed meal, the animals are injected with test article subcutaneously in the flank (0 min) with a Terumo insulin syringe (0.5 mL, ½" needle). All study animals have ad libitum access to clean, fresh water throughout the remaining blood collection period.

Serial blood samples (2.0 mL each) are collected from each animal at the following time points: −30, −20 (then immediately Fed), 0 (just before dose), 5, 10, 15, 30, 45, 60, 75, 90, 105, 120, 150, 180, 240, and 360 minutes following the SC dosing. Blood samples (anticoagulant: none [serum]) were maintained at ambient temperature for at least 30 minutes but no more than 2 hours to allow for clotting. Serum is then separated by centrifugation and divided into two aliquots and stored frozen at approximately −70° C. Aliquots are shipped on dry ice by a next day shipping service.

Serum insulin concentrations are determined using a competitive radioimmunoassay (RIA), as described above. Data are analyzed utilizing non-compartmental pharmacokinetic analysis using Phoenix WinNonLin 6.3, as described above. Serum glucose concentrations are determined using an automated Cobas c311 Clinical Chemistry Analyzer (Roche Diagnostics, Indianapolis, Ind.).

Serum glucose results (mg/dL) are given in Table 6 below.

TABLE 6

Serum glucose results (mg/dL).

| Time (min) | HUMALOG | | Formulation C insulin lispro + 5 mM triphosphate | | Formulation D insulin lispro + 10 mM triphosphate | | Formulation E insulin lispro + 20 mM triphosphate | |
|---|---|---|---|---|---|---|---|---|
| | Average | St. dev. | Average | St. dev. | Average | St. dev. | Average | St. dev. |
| −30 | 287 | 63 | 266 | 49 | 283 | 43 | 285 | 34 |
| −20 | 299 | 65 | 275 | 52 | 295 | 40 | 292 | 37 |
| 0 | 306 | 65 | 280 | 54 | 294 | 43 | 299 | 43 |
| 5 | 314 | 64 | 281 | 53 | 294 | 43 | 300 | 49 |
| 10 | 320 | 61 | 252 | 47 | 266 | 39 | 256 | 52 |
| 15 | 314 | 59 | 221 | 45 | 232 | 40 | 215 | 56 |
| 30 | 305 | 65 | 161 | 50 | 171 | 44 | 146 | 59 |
| 45 | 277 | 73 | 141 | 57 | 141 | 47 | 114 | 59 |
| 60 | 246 | 74 | 126 | 64 | 126 | 60 | 99 | 61 |
| 75 | 219 | 73 | 113 | 63 | 113 | 60 | 96 | 63 |
| 90 | 183 | 76 | 106 | 73 | 102 | 57 | 92 | 63 |
| 105 | 160 | 71 | 95 | 63 | 99 | 57 | 96 | 63 |
| 120 | 140 | 72 | 82 | 60 | 94 | 55 | 93 | 60 |
| 150 | 117 | 72 | 77 | 52 | 81 | 51 | 96 | 58 |
| 180 | 105 | 80 | 77 | 59 | 72 | 48 | 106 | 71 |
| 240 | 133 | 93 | 115 | 83 | 99 | 67 | 163 | 101 |
| 360 | 219 | 93 | 164 | 94 | 163 | 94 | 197 | 92 |

PK parameters as a function of triphosphate concentration are given in Table 7 below.

TABLE 7

PK data.

| Formulation | | Tmax (min) | Cmax (nM) | $AUC_{INF}$ (min*nM) | CL/F (mL/min/kg) |
|---|---|---|---|---|---|
| Humalog | Mean ± SE | 58.8 ± 6.0 | 0.89 ± 0.098 | 127 ± 12 | 10.3 ± 0.89 |
| N = 12 | Median | 60 | 1.03 | 119 | 10.2 |
| Formulation C: | Mean ± SE | 52.5 ± 13.0 | 1.05 ± 0.093 | 132 ± 25 | 11.6 ± 1.5 |
| insulin lispro + 5 mM triphosphate N = 12 | Median | 37.5 | 1.12 | 120 | 9.97 |

TABLE 7-continued

PK data.

| Formulation | | Tmax (min) | Cmax (nM) | AUC$_{INF}$ (min*nM) | CL/F (mL/min/kg) |
|---|---|---|---|---|---|
| Formulation D: insulin lispro + 10 mM triphosphate N = 10 | Mean ± SE Median | 28.0 ± 10.6 15.0 | 1.23 ± 0.15 1.21 | 127 ± 29 98.6 | 12.0 ± 1.5 12.2 |
| Formulation E: insulin lispro + 20 mM triphosphate N = 12 | Mean ± SE Median | 12.9 ± 2.5 10.0 | 1.67 ± 0.14 1.84 | 116 ± 13 109 | 11.8 ± 1.2 11.0 |

Abbreviations: Tmax—time at maximal insulin concentration, Cmax—maximal insulin concentration, AUC$_{INF}$—area under the curve from 0 to infinity, CL/F—clearance/bioavailability Triphosphate at 5, 10, or 20 mM in formulations similar to HUMALOG accelerated time action and reduced Tmax and increased Cmax as compared with HUMALOG® and did so in a dose-dependent manner.

Study 3. Effect on Different Commercial Insulins

Fifteen diabetic (Alloxan induced), castrated, male Yucatan miniature swine with previously fitted vascular access ports are used to study the effect of triphosphate on the serum glucose and serum insulin time action profiles of different commercial insulins. Housing and nutrition of the animals and shipment and storage of the test and control articles are as described above in Studies 1 and 2.

Test articles (Formulations F, G and H in the table below) are formulated by adding sufficient triphosphate to commercial vials of HUMULIN-R®, NOVOLOG® and APIDRA® to reach a concentration of 20 mM triphosphate. Note that the concentrations of other ingredients listed in the table below reflect the concentrations of those ingredients in the commercial vials of those products; the concentrations have not been adjusted to account for the slight dilution resulting from the addition of triphosphate.

TABLE 8

Compositions of test and control articles.

| Formulation Name | Formulation Composition |
|---|---|
| HUMALOG | 3.5 mg/mL insulin lispro<br>7 mM sodium phosphate, pH 7.4<br>0.3 mM Zn<br>16 mg/mL glycerin<br>3.15 mg/mL m-cresol |
| Formulation F:<br>NOVOLOG +<br>20 mM<br>triphosphate | 100 Units/mL insulin aspart<br>19.6 mcg/mL zinc<br>16 mg/mL glycerin<br>1.50 mg/mL phenol<br>1.72 mg/mL m-cresol<br>1.25 mg/mL disodium hydrogen phosphate dehydrate<br>0.58 mg/mL sodium chloride<br>20 mM sodium triphosphate |
| Formulation G:<br>APIDRA +<br>20 mM<br>triphosphate | 100 units/mL insulin glulisine<br>3.15 mg/mL m-cresol<br>6 mg/mL tromethamine,<br>5 mg/mL sodium chloride<br>0.01 mg/mL polysorbate 20<br>20 mM sodium triphosphate |
| Formulation H:<br>HUMULIN +<br>20 mM<br>triphosphate | 100 units/mL insulin<br>16 mg/mL glycerin<br>2.6 mg/mL m-cresol<br>0.23 mM Zn<br>20 mM sodium triphosphate |

The study is a four-way cross over design allowing for each individual animal to receive each of the three test articles and the control by dosing one test article on each study date (4 dates each, 7 days apart). Animals are prepared for the study as described above with respect to Studies 1 and 2.

The animals are randomly placed into treatment groups (4 groups n=3-4 per group yields n=15 per treatment). One animal is excluded from the HUMULIN R+20 mM triphosphate and NOVOLOG+20 mM triphosphate groups due to port failure, yielding n=14 for those treatment groups. One animal is excluded from the HUMALOG group due to port failure and one animal is excluded from the HUMALOG group for not meeting inclusion criteria, yielding n=13 for that group.

Collection of baseline blood samples, injection with test articles, collection of blood samples and preparation, shipment and measurement of blood and serum samples are performed as described above with respect to Studies 1 and 2.

Serum glucose concentrations are determined using an automated AU480 Clinical Chemistry Analyzer (Beckman Coulter). Serum glucose results (mg/dL) are given in Table 9 below.

TABLE 9

Serum glucose results (mg/dL).

| Time (min) | HUMALOG Average | St. dev. | Formulation F: HUMULIN + 20 mM triphosphate Average | St. dev. | Formulation G: APIDRA + 20 mM triphosphate Average | St. dev. | Formulation H: NOVOLOG + 20 mM triphosphate Average | St. dev. |
|---|---|---|---|---|---|---|---|---|
| −30 | 343 | 39 | 335 | 62 | 336 | 45 | 343 | 56 |
| −20 | 360 | 38 | 356 | 64 | 350 | 45 | 355 | 58 |
| 0 | 372 | 43 | 368 | 61 | 366 | 42 | 367 | 48 |
| 5 | 386 | 37 | 371 | 63 | 378 | 39 | 373 | 51 |
| 10 | 362 | 39 | 315 | 64 | 307 | 37 | 296 | 50 |
| 15 | 348 | 39 | 274 | 65 | 276 | 45 | 255 | 50 |
| 30 | 274 | 65 | 209 | 73 | 201 | 63 | 177 | 56 |
| 45 | 239 | 82 | 187 | 85 | 169 | 76 | 139 | 59 |
| 60 | 190 | 90 | 184 | 101 | 143 | 76 | 118 | 67 |
| 75 | 173 | 82 | 185 | 110 | 130 | 79 | 113 | 76 |
| 90 | 150 | 77 | 175 | 115 | 114 | 67 | 105 | 82 |
| 105 | 136 | 67 | 164 | 118 | 104 | 64 | 103 | 84 |
| 120 | 129 | 68 | 164 | 124 | 102 | 68 | 102 | 82 |
| 150 | 116 | 67 | 145 | 123 | 94 | 68 | 94 | 78 |
| 180 | 111 | 73 | 134 | 122 | 91 | 65 | 92 | 71 |
| 240 | 131 | 80 | 120 | 108 | 107 | 65 | 103 | 74 |
| 360 | 174 | 101 | 116 | 111 | 149 | 86 | 149 | 88 |

Serum insulin concentrations are determined using a competitive radioimmunoassay (RIA), as described above with respect to Studies 1 and 2. Data are analyzed utilizing non-compartmental pharmacokinetic analysis using Phoenix WinNonLin. Pharmacokinetic parameters as a function of triphosphate concentration are given in Table 10 below.

TABLE 10

PK data.

| Formulation | | Tmax (min) | Cmax (nM) | $AUC_{INF}$ (min*nM) | CL/F (mL/min/kg) |
|---|---|---|---|---|---|
| HUMALOG N = 13 | Mean ± SE | 58.8 ± 7.49 | 1.12 ± 0.176 | 129 ± 9.27 | 9.88 ± 0.669 |
| | Median | 60 | 1.00 | 120 | 9.99 |
| Formulation F: HUMULIN + 20 mM triphosphate N = 14 | Mean ± SE | 22.5 ± 9.55 | 1.45 ± 0.230 | 173 ± 14.6 | 7.48 ± 0.527 |
| | Median | 7.50 | 1.12 | 159 | 7.54 |
| Formulation G: APIDRA + 20 mM triphosphate N = 15 | Mean ± SE | 17.7 ± 4.02 | 1.65 ± 0.196 | 166 ± 11.7 | 7.75 ± 0.527 |
| | Median | 10.0 | 1.52 | 153 | 7.85 |
| Formulation H: NOVOLOG + 20 mM triphosphate N = 14 | Mean ± SE | 27.9 ± 10.8 | 1.10 ± 0.111 | 121 ± 12.7 | 10.9 ± 0.784 |
| | Median | 12.5 | 0.980 | 108 | 11.1 |

Abbreviations: Tmax—time at maximal insulin concentration, Cmax—maximal insulin concentration, $AUC_{INF}$—area under the curve from 0 to infinity, CL/F—clearance/bioavailability.

The PK/PD data demonstrate that the use of triphosphate in formulations of various commercial insulins accelerated time-action and reduced Tmax as compared with HUMALOG with no triphosphate. All formulations containing 20 mM triphosphate caused faster Tmax as compared with HUMALOG alone. Formulations containing APIDRA and HUMULIN with 20 mM triphosphate caused higher Cmax as compared with HUMALOG alone.

Clinical Study

A clinical study is conducted to study the pharmacokinetic and pharmacodynamic effects of compositions of the present invention. The study is designed as a 5-period crossover study to compare the effects following subcutaneous (SC) doses of 4 formulations containing different concentrations of triphosphate with insulin lispro, as compared to a formulation of insulin lispro containing no triphosphate. Test articles are formulated by adding sufficient amounts of triphosphate and magnesium chloride to the U200 commercial formulation of insulin lispro to reach the concentrations indicated in Table 11 below:

TABLE 11

Compositions of test and control articles. In addition to insulin lispro, the U-200 HUMALOG formulation to which triphosphate and $MgCl_2$ are added to create the test articles also contains 5 mg/mL tromethamine, 16 mg/mL glycerin, 3.15 mg/mL m-cresol and 0.046 mg/mL $Zn^{2+}$.

| Formulation Name | Formulation Composition |
|---|---|
| HUMALOG | 100 units/mL insulin lispro |
| | 7 mM sodium phosphate |
| | 0.3 mM Zn |
| | 16 mg/mL glycerin |
| | 3.15 mg/mL m-cresol |
| Formulation I | +10 mM triphosphate |
| Formulation J | +20 mM triphosphate |
| Formulation K | +30 mM triphosphate |
| Formulation L | +30 mM triphosphate |
| | +7.5 mM $MgCl_2$ |

Healthy subjects are enrolled and each subject is randomized to a treatment sequence, comprising single 15 unit SC doses of insulin lispro alone and a single 15 insulin unit SC dose of each of the test formulations. A minimum of 3 days is required between dosing occasions for an individual subject.

Blood samples are collected at multiple time points to determine the serum concentrations of insulin lispro over time. Serum concentrations of insulin lispro are measured using a validated enzyme-linked immunosorbent assay method specific for insulin lispro. Pharmacokinetic analyses are conducted using standard noncompartmental methods of analysis using Phoenix® version 7.0 (or higher) and S-PLUS® software (version 8.2). Free serum insulin lispro concentrations are used to calculate pharmacokinetic parameters. Results are provided in Table 12 below.

TABLE 12

PK data.

| Treatment | | LS Mean | Ratio Test:Reference (95% CI) |
|---|---|---|---|
| $T_{onset}$ (min) | Humalog | 1.78 | |
| | Formulation I | 0.12 | 0.07 (0.04, 0.10) |
| | Formulation J | 0.10 | 0.05 (0.04, 0.08) |
| | Formulation K | 0.09 | 0.05 (0.03, 0.07) |
| | Formulation L | 0.08 | 0.04 (0.03, 0.07) |
| Early 50% $T_{max}$ (min) | Humalog | 19.06 | |
| | Formulation I | 6.04 | 0.32 (0.26, 0.38) |
| | Formulation J | 5.04 | 0.26 (0.23, 0.31) |
| | Formulation K | 4.73 | 0.25 (0.21, 030) |
| | Formulation L | 4.58 | 0.24 (0.20, 0.29) |
| $AUC_{(0-15\ min)}$ (pmol*h/L) | Humalog | 19.87 | |
| | Formulation I | 136.98 | 6.89 (5.44, 8.74) |
| | Formulation J | 155.78 | 7.84 (6.19, 9.93) |
| | Formulation K | 156.21 | 7.86 (6.21, 9.96) |
| | Formulation L | 157.25 | 7.92 (6.27, 10.00) |
| $AUC_{(0-30\ min)}$ (pmol*h/L) | Humalog | 120.07 | |
| | Formulation I | 371.42 | 3.09 (2.63, 3.64) |
| | Formulation J | 393.84 | 3.28 (2.79, 3.86) |
| | Formulation K | 397.06 | 3.31 (2.81, 3.89) |
| | Formulation L | 393.79 | 3.28 (2.79, 3.85) |
| Late 50% $t_{max}$ (min) | Humalog | 168.28 | |
| | Formulation I | 86.10 | 0.51 (0.45, 0.58) |
| | Formulation J | 82.10 | 0.49 (0.42, 0.57) |
| | Formulation K | 80.80 | 0.48 (0.44, 0.52) |
| | Formulation L | 84.52 | 0.50 (0.45, 0.56) |

Abbreviations: LS—least squares, CI—confidence interval, $T_{onset}$—time to onset of insulin appearance, early 50% $T_{max}$—time to early half-maximal drug concentration, $AUC_{(0-15\ min)}$—area under the curve from time zero to 15 minutes, $AUC_{(0-30\ min)}$—area under the curve from time zero to 30 minutes, late 50% $t_{max}$—time to late half-maximal drug concentration. P-value for all test articles compared to Humalog control <.0001.

The results show triphosphate-containing formulations have accelerated pharmacokinetic parameters as compared to the non-triphosphate-containing control.

In addition, a 5-hour euglycemic glucose clamp is conducted in each period to allow an assessment of glucodynamic response to each treatment. In this assessment the glucose infusion rate (GIR) over time is used as a measure of insulin effect. A locally weighted scatterplot smoothing (LOESS) function is applied to all individual GIR versus time profiles in each treatment group and/or period using S-PLUS software version 8.2. The fitted data for each subject are used to calculate glucodynamic parameters.

Analyses of the data show triphosphate-containing formulations have improved pharmacodynamic parameters as compared to the non-triphosphate-containing control. The studies described above demonstrate that addition of small quantities of certain polyphosphates such as pyrophosphate or triphosphate to insulin formulations can cause earlier Tmax and higher Cmax in the insulin pharmacokinetic profile.

Sequences
Human insulin A-chain
(SEQ ID NO: 1)
Gly Ile Val Glu Gln Cys Cys Thr Ser Ile Cys Ser Leu Tyr Gln Leu Glu Asn Tyr Cys Asn Human insulin B-chain
(SEQ ID NO: 2)
Phe Val Asn Gln His Leu Cys Gly Ser His Leu Val Glu Ala Leu Tyr Leu Val Cys Gly Glu Arg Gly Phe Phe Tyr Thr Pro Lys Thr.

Insulin lispro B-chain
(SEQ ID NO: 3)
Phe Val Asn Gln His Leu Cys Gly Ser His Leu Val Glu Ala Leu Tyr Leu Val Cys Gly Glu Arg Gly Phe Phe Tyr Thr Lys Pro Thr.

Insulin aspart B-chain
(SEQ ID NO: 4)
Phe Val Asn Gln His Leu Cys Gly Ser His Leu Val Glu Ala Leu Tyr Leu Val Cys Gly Glu Arg Gly Phe Phe Tyr Thr Asp Lys Thr.

Insulin glulisine B-chain
(SEQ ID NO: 5)
Phe Val Lys Gln His Leu Cys Gly Ser His Leu Val Glu Ala Leu Tyr Leu Val Cys Gly Glu Arg Gly Phe Phe Tyr Thr Pro Glu Thr.

We claim:

1. A pharmaceutical composition comprising an insulin and triphosphate, wherein the concentration of triphosphate is from about 10 to about 30 mM, provided that the composition does not contain a substituted anionic compound of non-saccharide structure, a saccharide multimer or EDTA.

2. The pharmaceutical composition of claim 1 wherein the concentration of triphosphate is from about 20 to about 25 mM.

3. The pharmaceutical composition of claim 1 wherein the concentration of triphosphate is about 20 mM.

4. The pharmaceutical composition of claim 1 further comprising zinc.

5. The pharmaceutical composition of claim 4 wherein the zinc concentration is from about 0.2 to about 5 mM.

6. The pharmaceutical composition of claim 1 further comprising a tonicity agent.

7. The pharmaceutical composition of claim 6 wherein the tonicity agent is glycerol.

8. The pharmaceutical composition of claim 1 further comprising one or more preservatives.

9. The pharmaceutical composition of claim 8, wherein the one or more preservatives are selected from the group consisting of phenol, meta-cresol, and benzyl alcohol.

10. The pharmaceutical composition of claim 1, wherein the insulin is selected from the group consisting of human insulin, insulin lispro, insulin aspart and insulin glulisine.

11. The pharmaceutical composition of claim 1, wherein the insulin concentration is from about 40 to about 500 IU/mL.

12. The pharmaceutical composition of claim 11, wherein the insulin concentration is from about 100 to about 200 IU/mL.

13. A method of treating diabetes comprising administering to a human in need thereof an effective dose of the pharmaceutical composition of claim 1.

14. An article of manufacture comprising the pharmaceutical composition of claim 1 wherein the article of manufacture is selected from the group consisting of a multiuse vial, a reusable pen injector, a pre-filled, disposable pen, an autoinjector, or a pump for CSII.

* * * * *

SEQUENCE LISTING

```
<160> NUMBER OF SEQ ID NOS: 5

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: synthetic construct

<400> SEQUENCE: 3

Phe Val Asn Gln His Leu Cys Gly Ser His Leu Val Glu Ala Leu Tyr
1               5                   10                  15
```

```
Leu Val Cys Gly Glu Arg Gly Phe Phe Tyr Thr Lys Pro Thr
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: synthetic construct

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: synthetic construct

<400> SEQUENCE: 5

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30
```